(12) United States Patent
Damron

(10) Patent No.: US 12,653,553 B2
(45) Date of Patent: Jun. 16, 2026

(54) SURGICAL GUIDE DEVICES AND SURGICAL CLAMPS INCLUDING SAME

(71) Applicant: The Research Foundation for the State University of New York, Albany, NY (US)

(72) Inventor: Timothy Damron, LaFayette, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 253 days.

(21) Appl. No.: 18/236,641

(22) Filed: Aug. 22, 2023

(65) Prior Publication Data

US 2024/0058022 A1 Feb. 22, 2024

Related U.S. Application Data

(60) Provisional application No. 63/399,748, filed on Aug. 22, 2022.

(51) Int. Cl.
*A61B 17/17* (2006.01)
(52) U.S. Cl.
CPC ...... *A61B 17/1796* (2013.01); *A61B 17/1742* (2013.01)

(58) Field of Classification Search
CPC .. A61B 17/17; A61B 17/1796; A61B 17/1742
See application file for complete search history.

(56) References Cited

U.S. PATENT DOCUMENTS

| | | | | |
|---|---|---|---|---|
| 4,444,180 A | * | 4/1984 | Schneider | A61B 17/1714 606/96 |
| 5,312,409 A | * | 5/1994 | McLaughlin | A61B 17/8847 606/86 R |
| 5,697,933 A | * | 12/1997 | Gundlapalli | A61F 2/0811 606/206 |
| 2010/0082035 A1 | * | 4/2010 | Keefer | A61B 17/1666 606/91 |
| 2021/0015503 A1 | * | 1/2021 | Arciero | A61B 17/1796 |
| 2021/0244478 A1 | * | 8/2021 | Richter | A61B 90/06 |

* cited by examiner

*Primary Examiner* — Christian A Sevilla
(74) *Attorney, Agent, or Firm* — Garrett M. Smith

(57) ABSTRACT

A combined drill guide and suture passer for use in assisting repair of the posterior hip capsule and short external rotators following posterior approach total hip arthroplasty. The device is a sterilizable metallic surgical instrument for repetitive use during a total hip surgical procedure. The device can be embodied as surgical guide for drilling and suturing, or can be embodied as a clamp including the surgical guide.

14 Claims, 11 Drawing Sheets

120

124

126

128

130

130

128

122

126

126

SURGICAL GUIDE DEVICES AND SURGICAL CLAMPS INCLUDING SAME

CROSS-REFERENCE TO RELATED APPLICATION

This application claims the benefit of U.S. Provisional Application No. 63/399,748, filed Aug. 22, 2022, the entirety of which is hereby incorporated herein by this reference.

BACKGROUND OF THE INVENTION

1. Field of the Invention

The present invention generally relates to surgical devices. More particularly, the present invention relates to surgical guide device used during both a drilling process and a suturing process performed during soft tissue repair surgical procedures on hips.

2. Description of the Related Art

A posterior approach to the human hip for total hip replacement as well as trauma (acetabular posterior column fixation), pediatric orthopedic surgery, and tumors is a common surgical approach. The posterior approach has been historically and remains the most common approach for total hip arthroplasties, of which there are currently about 450,000 per year in the US. The first step in this surgical approach is repair of the soft tissues over the hip joint, which is a key step in total hip replacement because of the risk of total hip dislocation.

To minimize risk of posterior hip dislocation following placement of a total hip arthroplasty (a 4% overall risk) using a posterior approach, the soft-tissues in the region of surgical exposure, including the short external rotators (pyriformis, superior and inferior gemelli, obturator oblique, +/−quadratus femoris) and the remaining hip capsule are repaired. This is commonly done by passing sutures through the bone of the greater trochanter on the posterior aspect so that the sutures can be tied over the "top" (lateral aspect) of that portion of the femur. This secures the soft tissue structures solidly so that the prosthetic ball is less likely to dislocate out of the prosthetic cup (acetabular liner).

The performance of this step of the procedure is a problem with the posterior approach because a good repair, as currently done, adds significant time to the procedure. Using standard techniques, the appropriate execution of this step is awkward and operator dependent (easier for those with the most experience), but still variable in difficulty and success of achieving a solid repair, given the lack of a devoted instrument.

There is accordingly a lack of a devoted medical instrument to assist in accomplishing the goals of this specific part of the total hip procedure. It is thus to an improved medical device for hip arthroplasties that the present invention is primarily directed.

BRIEF SUMMARY OF THE INVENTION

Briefly described, the present invention provides a combined drill guide and suture passer for use in assisting repair of posterior hip capsule and short external rotators (soft tissue repair) following posterior approach total hip arthroplasty. It is a sterilizable metallic surgical instrument for repetitive use during total hip surgical procedure. The invention thus includes a hand-held medical device similar to other standard surgical instruments, but uniquely adapted for this hip procedure purpose.

In a first aspect of the disclosure, the invention includes a surgical guide device having a body including a support portion, a plurality of guide portions extending from the support portion, with each of plurality of guide portions spaced apart from one another. There are a plurality of apertures extending through the support portion and a single guide portion of the plurality of guide portions.

A second aspect of the disclosure provides a surgical clamp with a first arm including a retention component, and a second arm coupled to the first arm, the second arm include a surgical guide device formed thereon, adjacent the retention component. The surgical guide device includes a body having a support portion, a plurality of guide portions extending from the support portion with each of plurality of guide portions spaced apart from one another, and a plurality of apertures each extending through the support portion. There is a single guide portion of the plurality of guide portions.

The present invention therefore provides an advantage in a surgical device that is specialized to perform hip arthroplasty surgeries. The present invention thus has an industrial application in medical device production. Other advantages and applications of the present invention would be apparent to one of skill in the art after review of the present specification and drawings.

DETAILED DESCRIPTION OF THE INVENTION

Figure 1:
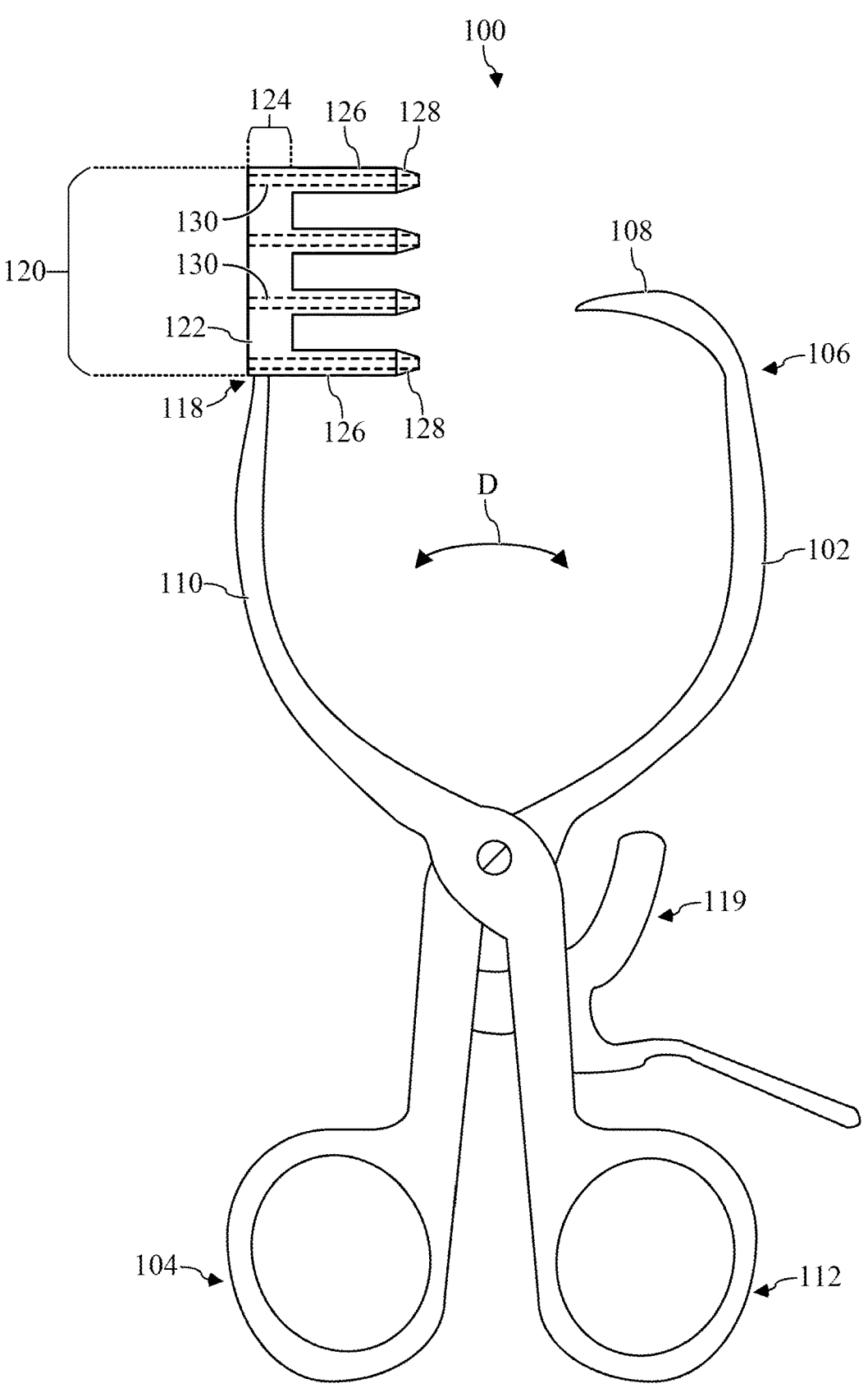
FIG. 1 shows a front view of one embodiment of a surgical clamp including a surgical guide device.

With reference to the figures in which like numerals represent like elements throughout the several views, FIG. 1 shows a front view of a surgical bone clamp 100. In a non-limiting example, surgical clamp 100 may be formed as a pointed bone surgical clamp. However, it is understood that surgical clamp 100 may be formed has any suitable surgical clamp that may be used in procedures that include drilling processes and/or soft tissue repair surgical procedure, as discussed herein. For example, surgical clamp 100 may also be formed as a modified angled Lowman-type bone clamp, a Bargo bone holding clamp, a speed-lock bone clamp, a browner MIS bone clamp, a Cannestra trochanteric fracture reduction clamp, a Chen diaphyseal fracture reduction clamp, a Desai Jones fracture reduction clamp, a Durham bone reduction clamp, a Durkan ratchet bone clamp, and the like.

As shown in FIG. 1, surgical clamp 100 may include a first arm 102. In the non-limiting example first arm 102 may include a handle end 104, and operation end 106 positioned opposite handle end 104. First arm 102 may also include a retention component 108, or other retention means. More specifically, and as shown in FIG. 1, first arm 102 of surgical clamp 100 may include retention component 108 formed at, adjacent to, and/or on operation end 106. Retention component 108 may be formed as any suitable component, portion, and/or configuration that may contact a portion of the patient (e.g., bone) and aid in the retention and/or coupling of surgical clamp 100 to the portion of the patient during the surgical procedure using surgical clamp 100 (see, FIG, 4). In the non-limiting example, retention component 108 may be formed as a surgical spike having a pointed end that may contact and/or press against a portion of the patient during the surgical procedure using surgical clamp 100. In other non-limiting examples, retention component 108 may be formed or include any suitable configuration or means that may aid in the clamping, contouring, and/or contacting of the bone undergoing the repair process, discussed herein.

Surgical clamp 100 may also include a second arm 110. Second arm 110 may be positioned adjacent to first arm 102. More specifically, second arm 110 may be positioned adjacent to and/or at least partially opposite first arm 102. Additionally, second arm 110 may substantially cross over and/or overlap a portion of first arm 102. In the non-limiting example shown in FIG. 1 second arm 110 and first arm 102 may be pivotably coupled. That is, first arm 102 may be pivotably coupled to second arm 110 at the point of overlap/intersection in order to adjust the distance between first arm 102 and second arm 110 by moving first arm 102/second arm 110 in a direction (D). Similar to first arm 102, second arm 110 includes a handle end 112, and operation end 118 positioned opposite handle end 112.

Additionally as shown, surgical clamp 100 may also include a locking mechanism 119. Locking mechanism 119 may be coupled to first arm 102 and second arm 110, respectively. That is, at least a portion of locking mechanism 119 may be coupled to, positioned on, and/or formed integrally with each of first arm 102 and second arm 110 of clamp 100. Locking mechanism 119 may be formed from any suitable component or mechanical mechanism that may aid in the locking or retaining of surgical clamp 100 in a desired, fixed position. This in turn may ensure clamp 100 remains coupled to the bone being repaired during the surgical procedure discussed herein. In the non-limiting example shown in FIG. 1, locking mechanism 119 may be formed as a ratcheted surface mechanism. In other non-limiting examples, locking mechanism 119 may be formed as any other suitable mechanism including, but not limited to, a threaded "speed lock," a flip-over ratcheted surface bar, or the like.

Surgical clamp 100, and more specifically first arm 102 and second arm 110 may be formed from any suitable material that may be used to perform surgical procedures, as well as be sterilized/maintain sterilization. For example, first arm 102 and second arm 110 of surgical clamp 100 may be formed from metal, metal-alloys, and/or ceramic material. Furthermore, although shown as two distinct portions, components, and/or arms, it is understood that surgical clamp 100 may be formed as single/integral device including integrally formed first arm 102 and second arm 110.

In the non-limiting example shown in FIG. 1, surgical clamp 100 may also include a surgical guide device 120, or other surgical guide means. Surgical guide device 120 may be positioned on second arm 110. More specifically, surgical guide device 120 may be positioned on, formed on, and/or included in second arm 110, adjacent retention component 108 of first arm 102. Additionally, surgical guide device 120 may be positioned on operation end 118 of second arm 110. In non-limiting examples, surgical guide device 120 may be formed integral with second arm 110 of surgical clamp 100, or surgical guide device 120 may be (distinct from) and releasably coupled to second arm 110 of surgical clamp 100. In the latter example, surgical guide device 120 may be releasably coupled to operation end 118 of second arm 110 using any suitable coupling or fastening component including, but not limited to, screws, bolts-and-nuts, rivets, snap-fit, retention bands, fastening pins, or the like.

Figure 2:
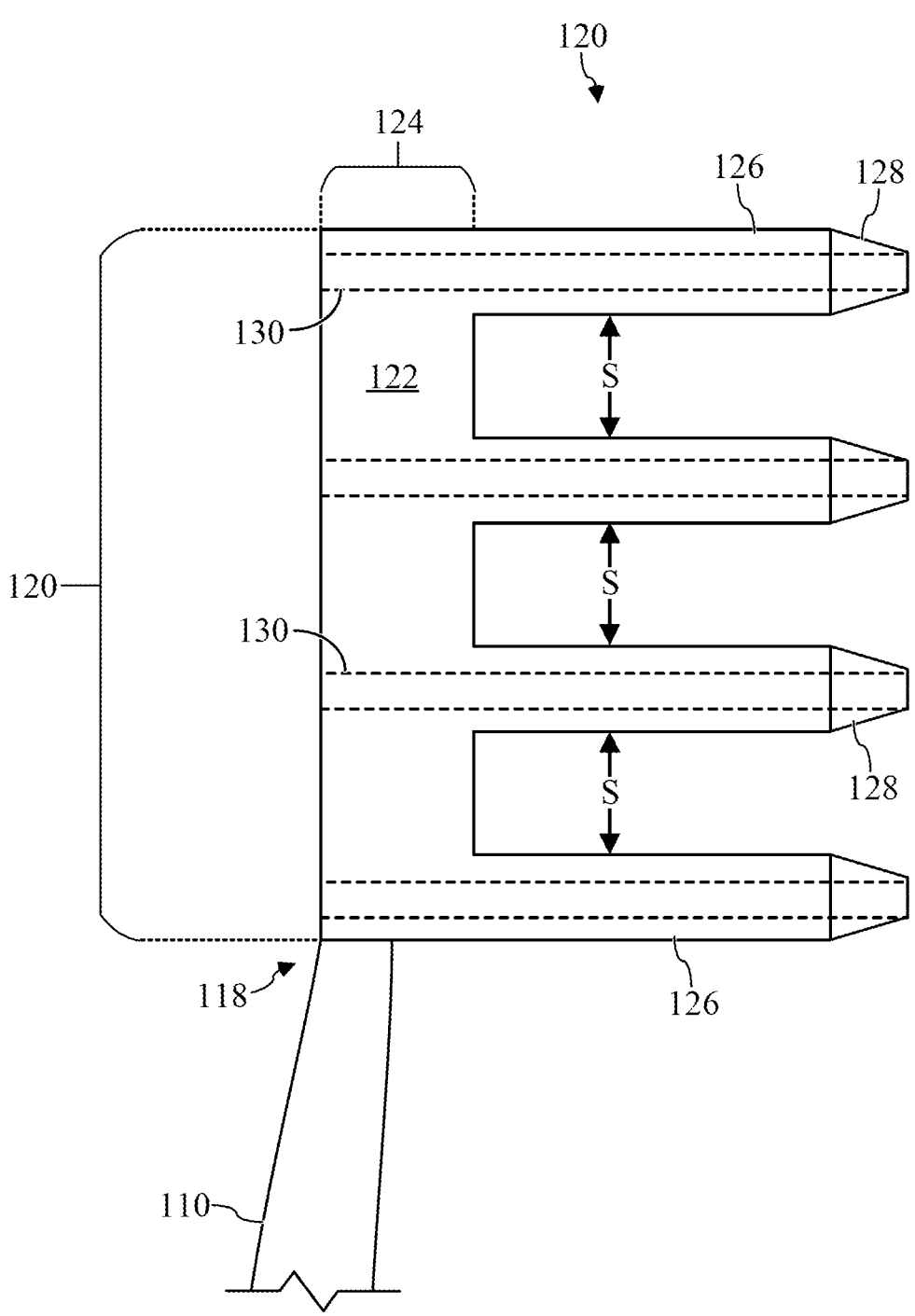
FIG. 2 shows an enlarged front view of the surgical guide device of FIG. 1.
Figure 3:
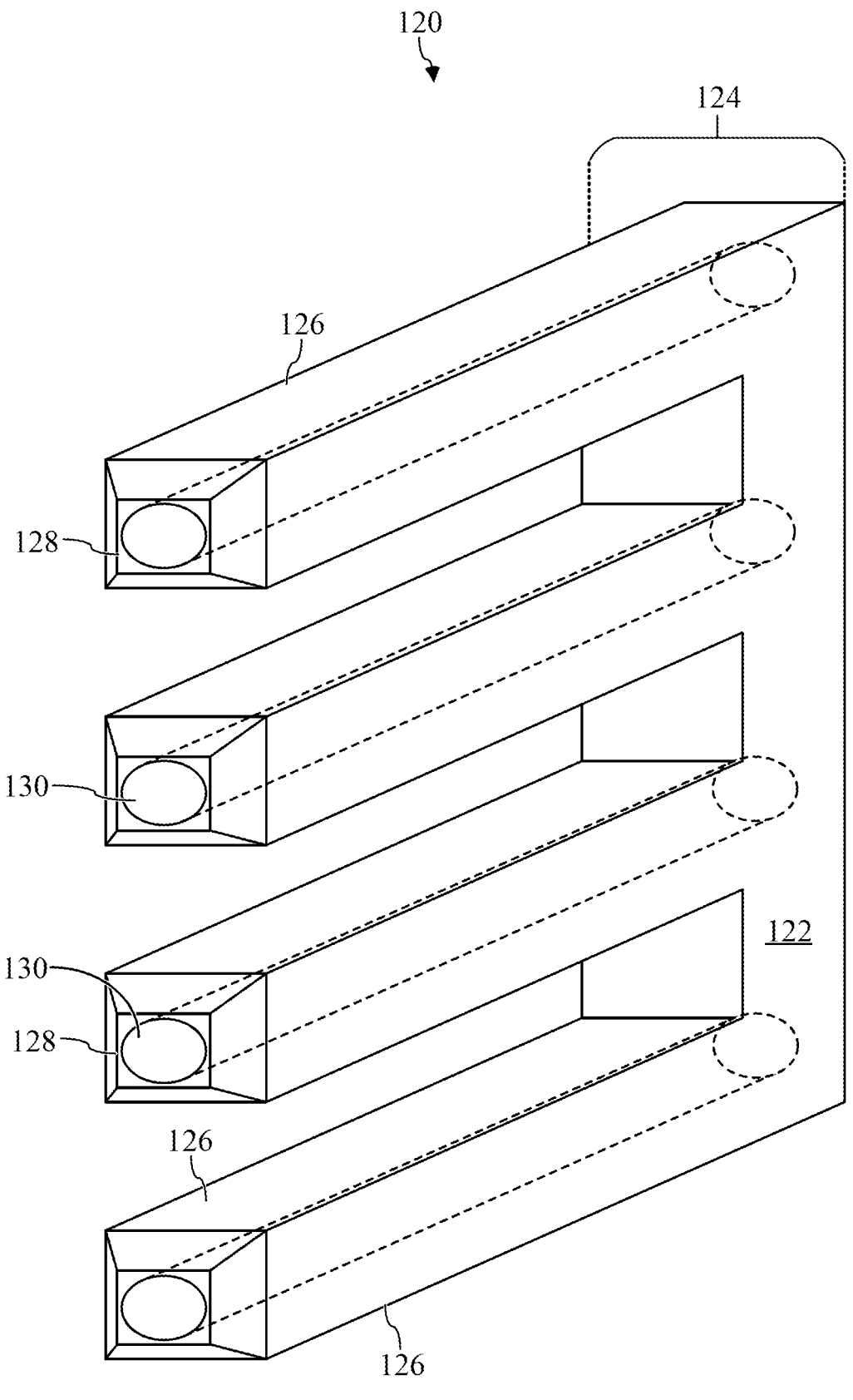
FIG. 3 shows an enlarged perspective view of the surgical guide device of FIG. 1.

Turning to FIGS. 2 and 3, and with continued reference to FIG. 1, additional features of surgical guide device 120 may be discussed. As shown in FIGS. 1-3, surgical guide device 120 may include and/or be formed from a body 122. Body 122 of surgical guide device 120 may include a support portion 124. In non-limiting examples, support portion 124 may be formed integral with or may be coupled directly to second arm 110 of surgical clamp 100. Support portion 124 may also extend from second arm 110 of surgical clamp 100, substantially opposite retention component 108 formed on first arm 102.

Body 122 may also include a plurality of guide portions 126 extending from support portion 124, or other surgical tool guide means. In the non-limiting example shown herein, each of the plurality of guide portions 126 may extend substantially perpendicular from support portion 124. In other non-limiting examples, the plurality of guide portions 126 may extend from support portion 124 at a predetermined and/or desired angle. In addition to extending from support portion 124, each of the plurality of guide portions 126 may be spaced apart from one another. That is, a space (S) may be formed between each of the plurality of guide portions 126 of body 122 forming surgical guide device 120. In the non-limiting example shown in FIGS. 1-3, that space (S) between each of the plurality of guide portions 126 may be substantially uniform and/or the same. In other non-limiting examples (e.g., FIG. 11), a space between two of the plurality of guide portions 126 may be distinct from another space between two distinct guide portions of the plurality of guide portions 126. As shown, guide portions 126 may be formed integral with support portion 124. More specifically, each of the plurality of guide portions 126 of surgical guide device 120 may be integrally formed with support portion 124. In other non-limiting example, guide devices 120 may be distinct from and/or releasably coupled to support portion 124 of surgical guide device 120.

Although four guide portions 126 are shown in FIGS. 1-3, it is understood that the number of guide portions 126 included in body 122 for surgical guide device 120 is illustrative. As such, body 122 of surgical guide device 120 may include more or less guide portions 126 (see, FIG. 7).

Body 122 of surgical guide device 120 may also include tapered distal ends 128. More specifically, each of the plurality of guide portions 126 of body 122 may include tapered distal end 128 formed opposite support portion 124.

Tapered distal ends 128 may narrow and/or reduce the size/dimension of guide portions 126 to decrease the spatial footprint of surgical guide device 120 and/or increase a force applied to a portion of the patient to ultimately maintain contact/the coupling between surgical guide device 120 and the portion of the patient during the procedure, as discussed herein. Although shown as including tapered distal end 128, it is understood that surgical guide device 120 may not include tapered distal end 128 (see, FIG. 8).

As shown in FIGS. 1-3, body 122 of surgical guide device 120 may also include a plurality of apertures 130. Each of the plurality of apertures 130 may extend through support portion 124 and a single, corresponding guide portion 126 of the plurality of guide portions 126. That is, surgical guide device 120 may include a plurality of apertures 130, where each aperture 130 extends through a corresponding guide portion 126 of the plurality of guide portions 126. As such, and as shown in the non-limiting example of FIGS. 1-3, surgical guide device 120 including four distinct guide portions 126 may include four distinct apertures 130 as well. Each of the plurality of apertures 130 of surgical guide device 120 may be sized to receive a surgical drill (see, FIG. 4) when performing the surgical procedure as discussed herein.

Additionally, each of the plurality of apertures 130 of surgical guide device 120 may be sized to receive at least one of a suture passer including a surgical suture (see, FIG. 5) or the surgical suture including a needle (not shown). Furthermore, there can be a channel within guide portions 126 parallel to aperture 130 such that the ends of the suture could be accessed and tied without necessarily removing the clamp 100 from its position on the bone.

Body 122 of surgical guide device 120 for surgical clamp 100 may be formed from any suitable material that may be used to perform surgical procedures, as well as be sterilized/ maintain sterilization. For example, body 122 of surgical guide device 120, including all components, devices, and/or portions included therein, may be formed from a metal alloy material, a polymer material, or a ceramic material. And the guide portions 126 can square, rectangular, round, or virtually any shape in cross-section.

Figure 4:
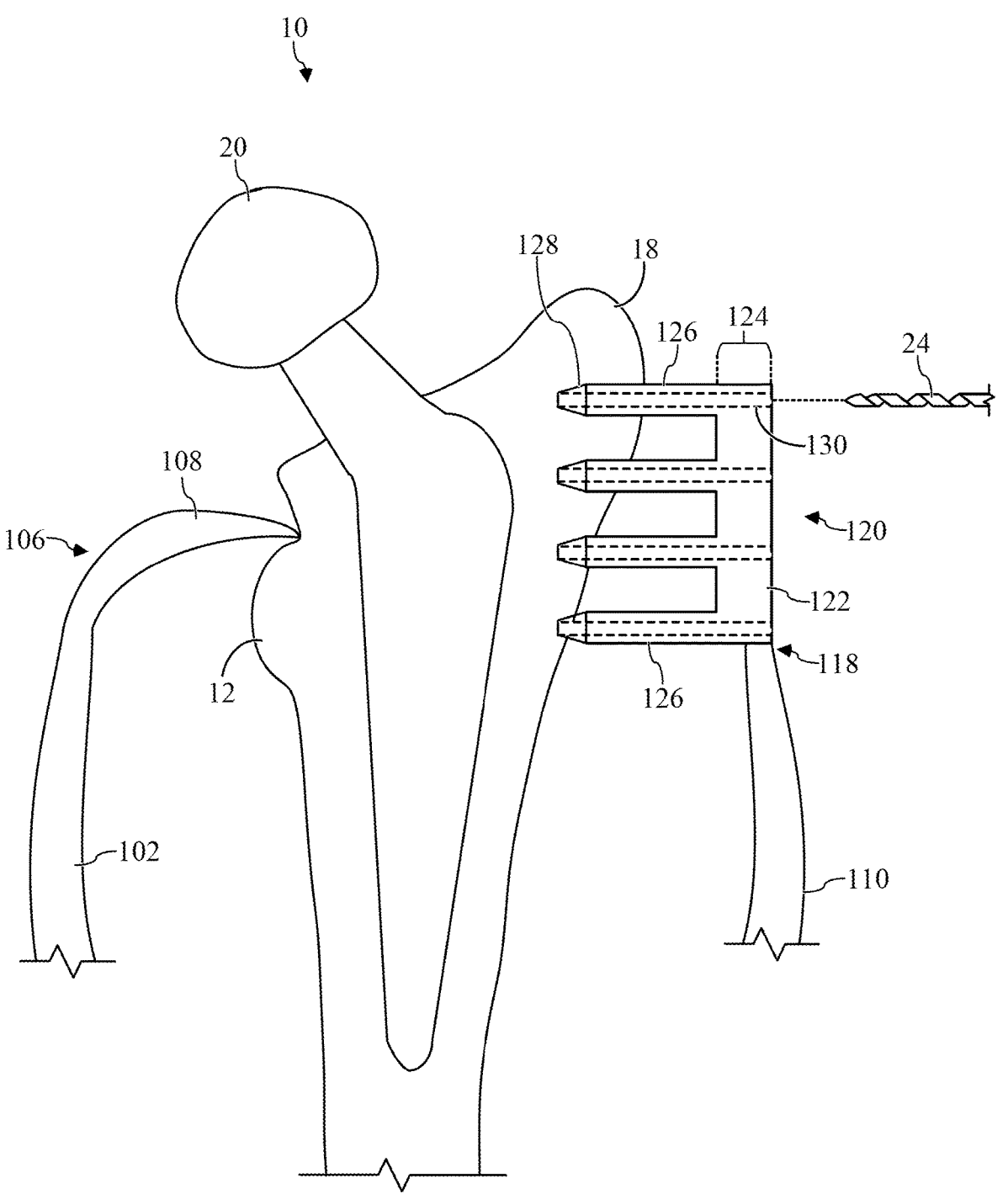
FIG. 4 shows a front view of the surgical clamp in situ including the surgical guide device positioned on a femur bone, with a drill bit in use.
Figure 5:
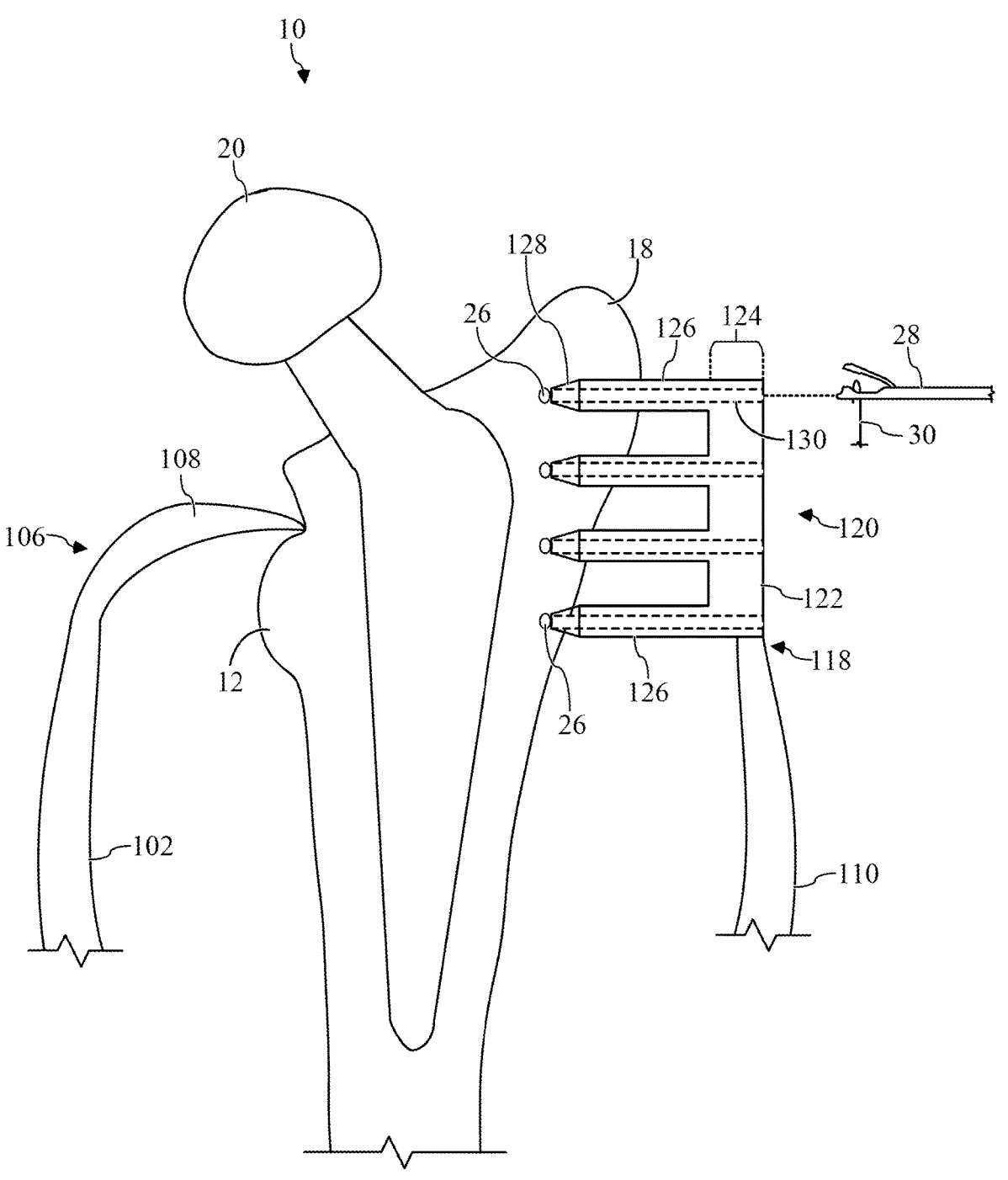
FIG. 5 shows a front view of the surgical clamp of FIG. 4, including the surgical guide device positioned on a femur bone with a suture passer in use.
Figure 6:
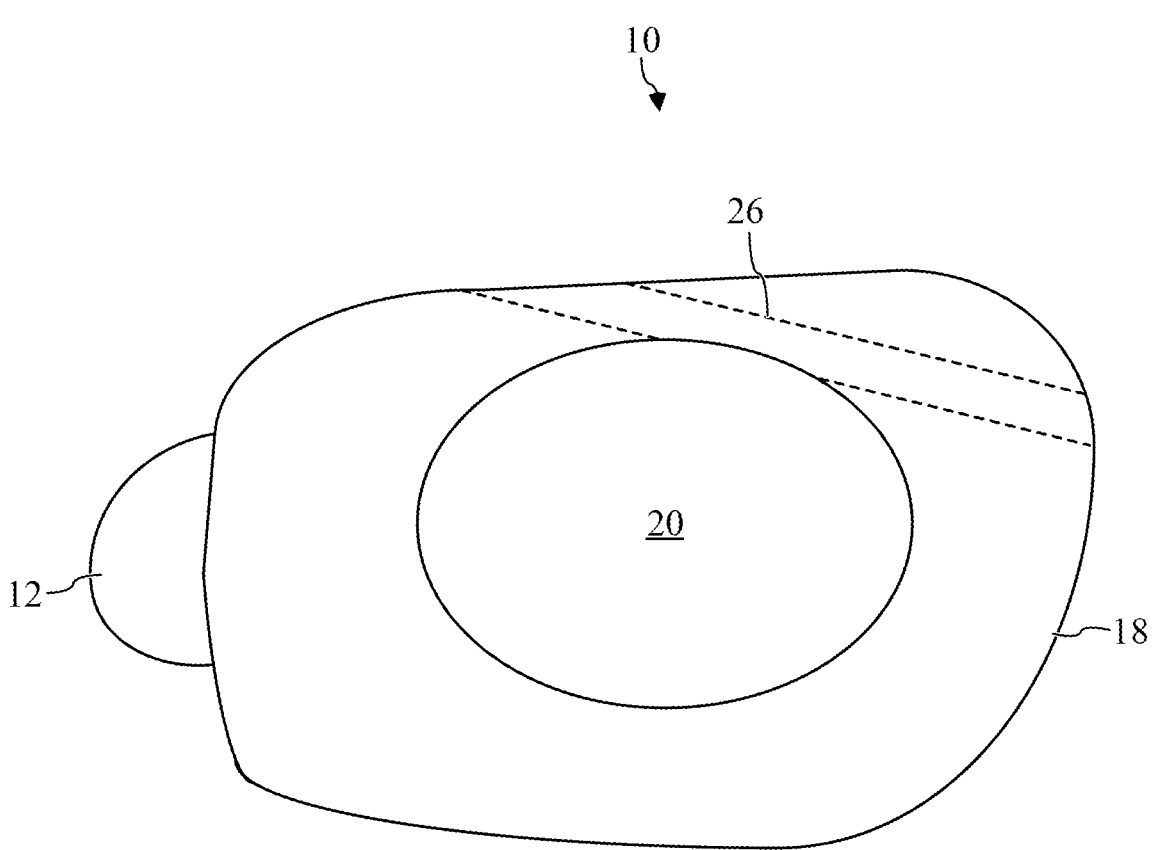
FIG. 6 shows a top view of the femur bone of FIGS. 4 and 5, including a surgical hole formed therein using the surgical guide device of the surgical clamp.

Turning to FIGS. 4-6, a process of performing a surgical procedure on a patient using surgical clamp 100 may be shown. That is, FIGS. 4-6 may depict a portion of a patient undergoing surgical processes using surgical clamp 100. It is understood that similarly numbered and/or named components may function in a substantially similar fashion. Redundant explanation of these components has been omitted for clarity.

In the non-limiting example shown in FIGS. 4-6, a patient's femur 10 may undergo surgical processes such repairing posterior hip capsule and short external rotators (e.g., soft tissue repair) following posterior approach total hip arthroplasty. FIGS. 4-6 may depict an upper portion (e.g., hip adjacent portion) of the patient's femur 10 including, amongst other portions, a lesser trochanter 12, a greater trochanter 18, and a head 20 of a femoral component or implant 22.

During the process or procedure, surgical clamp 100 may be coupled to, positioned on, and/or affixed to femur 10. More specifically, and as shown in FIG. 4, retention component 108 of first arm 102 may contact, be positioned on, and/or apply a force to lesser trochanter 12 of femur 10. Additionally, surgical guide device 120 of second arm 110 may contact, be positioned adjacent to, and/or apply a force to a portion of femur 10 formed below greater trochanter 18. In the non-limiting example, tapered distal end 128 of each of the plurality of guide portions 126 for surgical guide device 120 may also contact and/or be positioned on the portion of femur 10 formed below greater trochanter 18. As such, a portion of femur 10 contacted by surgical guide device 120 may be exposed to the plurality of apertures 130 formed in surgical guide device 120. During the procedure, a surgical drill 24 may be operated and inserted through each of the plurality of apertures 130 to form holes 26 (see, FIGS. 5 and 6) through femur 10. Other surgical tools can be placed through the apertures as would be known to one of skill in the art. The use of surgical clamp 100 including surgical guide device 120 may aid in forming straight, properly aligned/angled, and evenly (or desirably) spaced holes 26 in femur 10 during the repair process discussed herein.

Although usually the surface of the greater trochanter 18 is fairly flat to seat the tapered distal end 128 of each of the guide portions 126 onto the bone, the surface can be more oblique or vary in profile. Furthermore, a mobile articulation (not shown), such as a universal joint or other coupler, can be placed between the surgical guide device 120 and second arm 110. Alternately or in combination, there can be an additional surgical spike (not shown) of the retention component 108 and affixed to the second arm 110 close to or at the level of surgical guide device 120. This, the spikes on both would provide the stability and even if the tape or distal ends 128 were not evenly in contact with the surface of the greater trochanter 18, they would still be adequately rigidly fixed.

In addition to forming holes 26 in femur 10 with the desired characteristics, surgical guide device 120 may also aid in performing suturing processes during the medical procedure. That is, surgical guide device 120 of surgical clamp 100 may not only work as a drill guide but may also assist the surgeon/physician when performing suturing processes during the repair procedure discussed herein.

Turning to FIG. 5, after holes 26 are formed in femur 10, surgical clamp 100 may remain coupled, attached, and/or affixed to femur 10. The attending surgeon/physician may then pass a suture passer 28, as an exemplary surgical tool, including a surgical suture 30 through each of the plurality of apertures 130 formed in surgical guide device 120 to more accurately and/or under improved control provide sutures to the patient/femur 10. In the non-limiting example, suture passer 28 may extend through apertures 130 of surgical guide device 120 and directly into holes 26 formed in femur 10 with additional ease and/or accuracy. Although shown as including a suture passer 28, surgical suture 30 could include a needle (not shown) that may also be placed into each aperture 130 of surgical guide device 120 such that a portion of the suture that would be pulled through surgical aperture 130 with the end of the suture.

In an embodiment, a simplified process would be to use a drill bit 24 with a hole near the tip (not shown) that is threaded like the eye and the needle such that it can serve the dual purposes of drill bit 24 and suture passer 28. In such embodiment, this eliminates the need to thread the suture passer through aperture 130 after pulling out the drill bit 24.

With reference to FIG. 6, there can be a cross-section through the intertrochanteric portion of the proximal femur with the greater trochanter 18 and the lesser trochanter 12 on the corresponding surfaces and the hole 26 being oriented as to avoid the intramedullary portion of the head 20 of a femoral component or implant 22. There will be a thick outer cortex with the inner border of that cortex being approximately parallel to all of the surfaces of the outer cortex. The hole 26 typically passes completely through the greater trochanteric cortex, entering and through the medullary bone adjacent to the cross-section of the femoral component, and then exiting through the second cortex.

Figure 7:
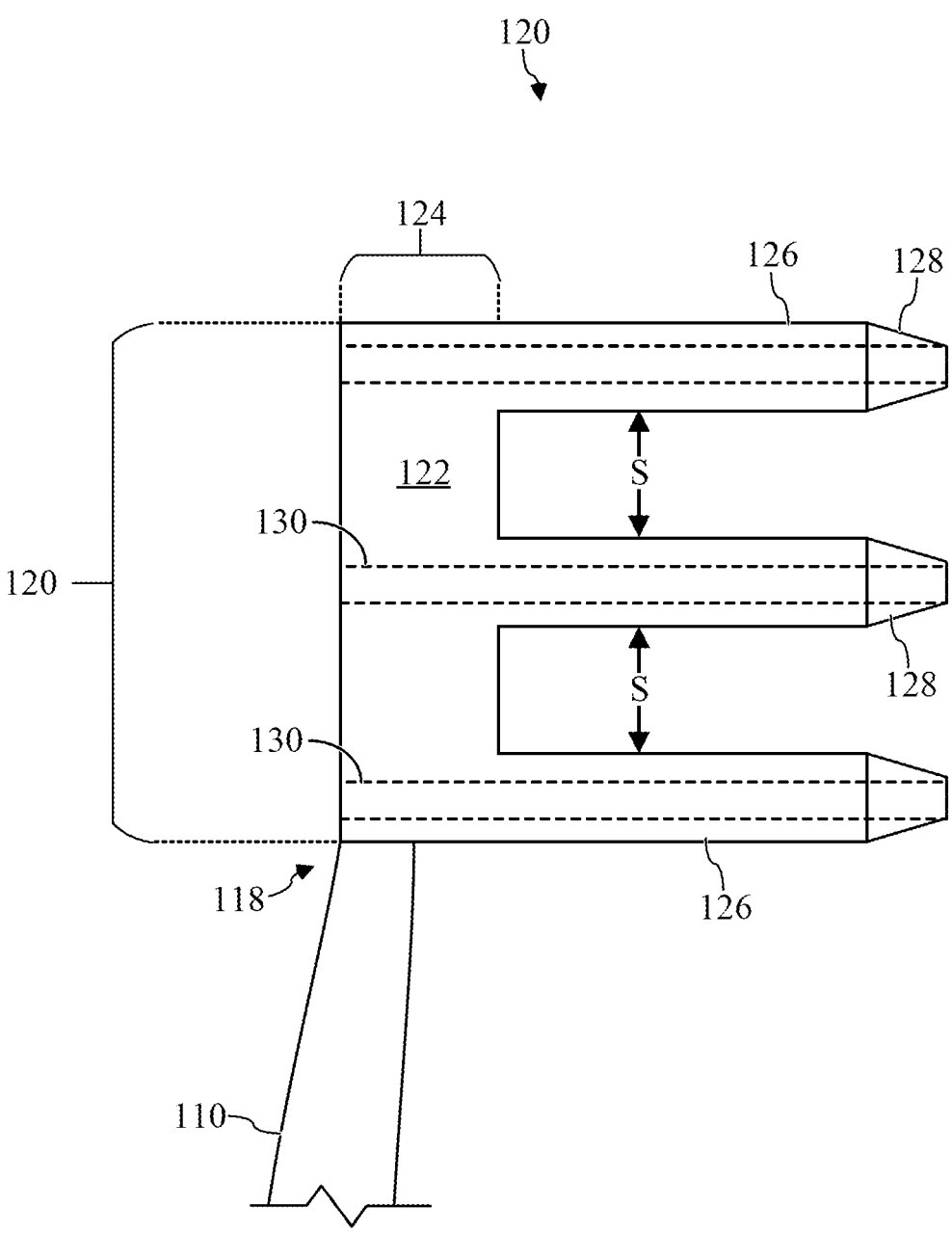
FIG. 7 shows an enlarged front view of an embodiment of surgical guide devices.
Figure 8:
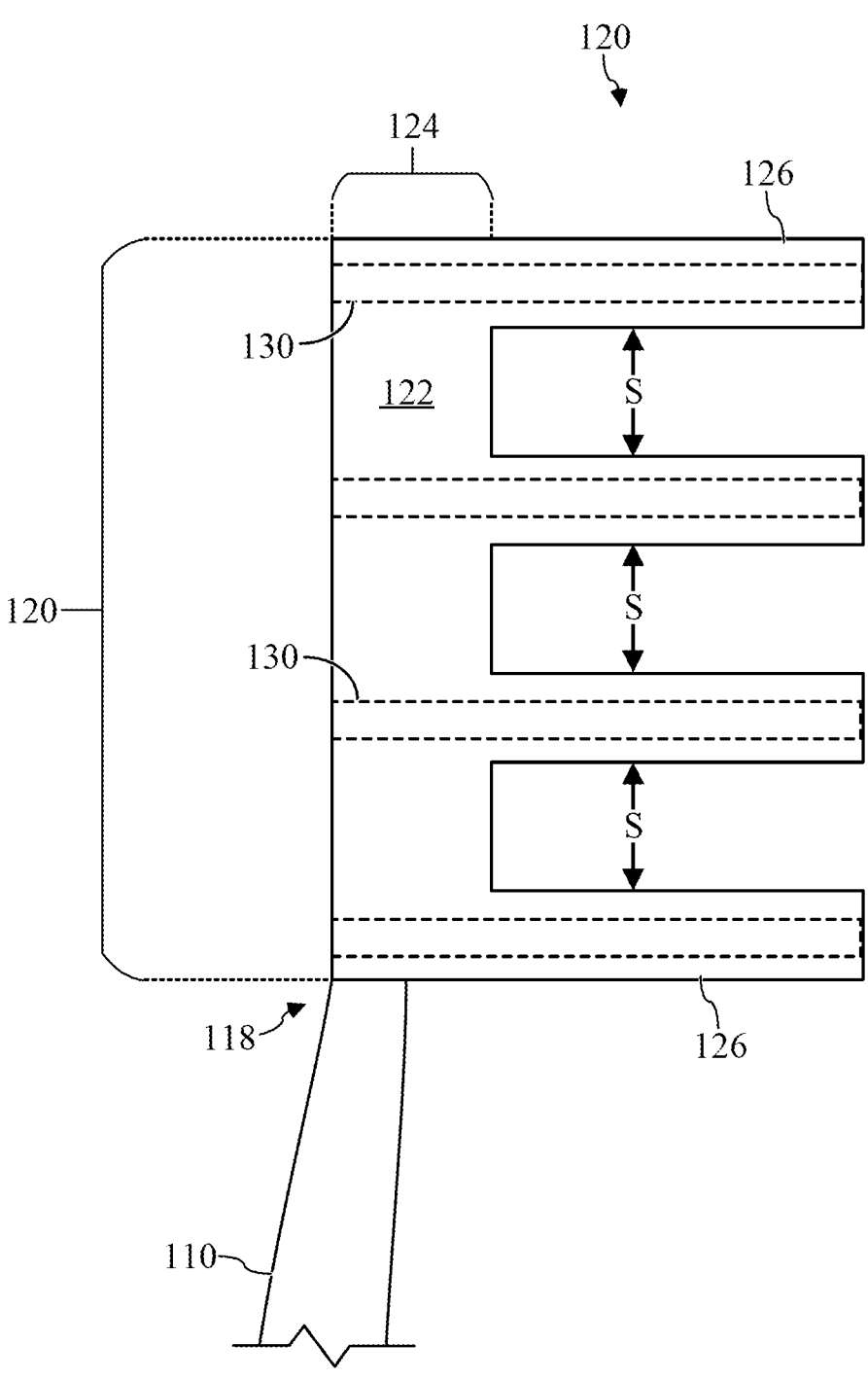
FIG. 8 shows an enlarged front view of an embodiment of surgical guide devices.
Figure 9:
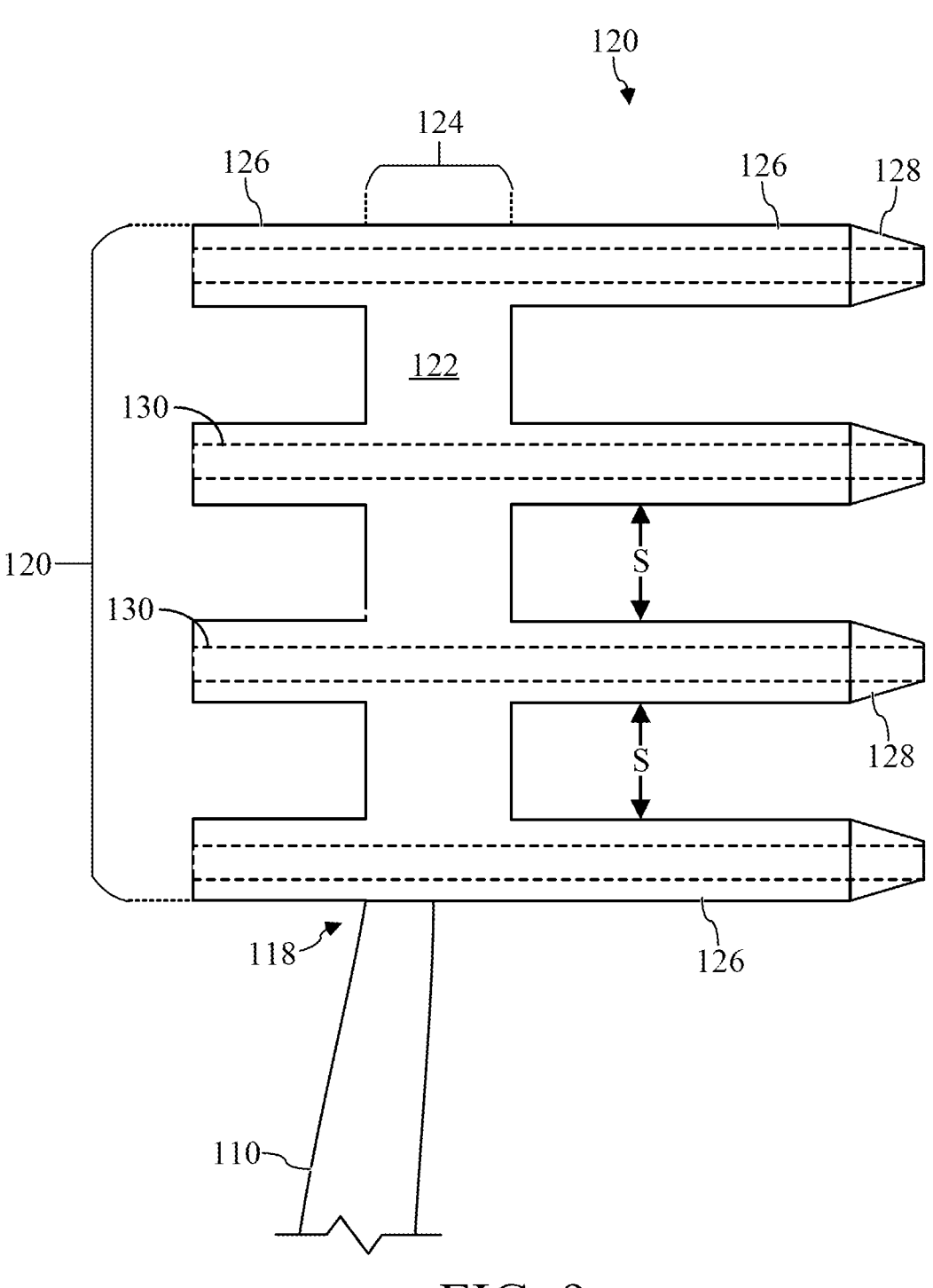
FIG. 9 shows an enlarged front view of an embodiment of surgical guide devices.

Turning to FIGS. 7-9, additional non-limiting examples of surgical guide device 120 may be depicted. As discussed herein, surgical guide device 120 may be formed on and/or included in surgical clamp 100. It is understood that similarly numbered and/or named components may function in a substantially similar fashion. Redundant explanation of these components has been omitted for clarity. As shown in FIG. 7, surgical guide device 120 of surgical clamp 100 may include three guide portions 126 and/or three apertures 130 extending through surgical guide device 120.

FIG. 8 shows another non-limiting example of surgical guide device 120. In the non-limiting example, surgical guide device 120 of surgical clamp 100 may not include tapered distal ends 128 formed on guide portion 126.

In the non-limiting example shown in FIG. 9, the plurality of guide portions 126 may extend on either side of support portion 124. More specifically, each guide portion 126 of the plurality of guide portions 126 of surgical guide device 120 may extend on opposite sides of support portion 124. As such, a section of each guide portion 126 may extend from support portion 124 opposite tapered distal end 128.

Figure 10:
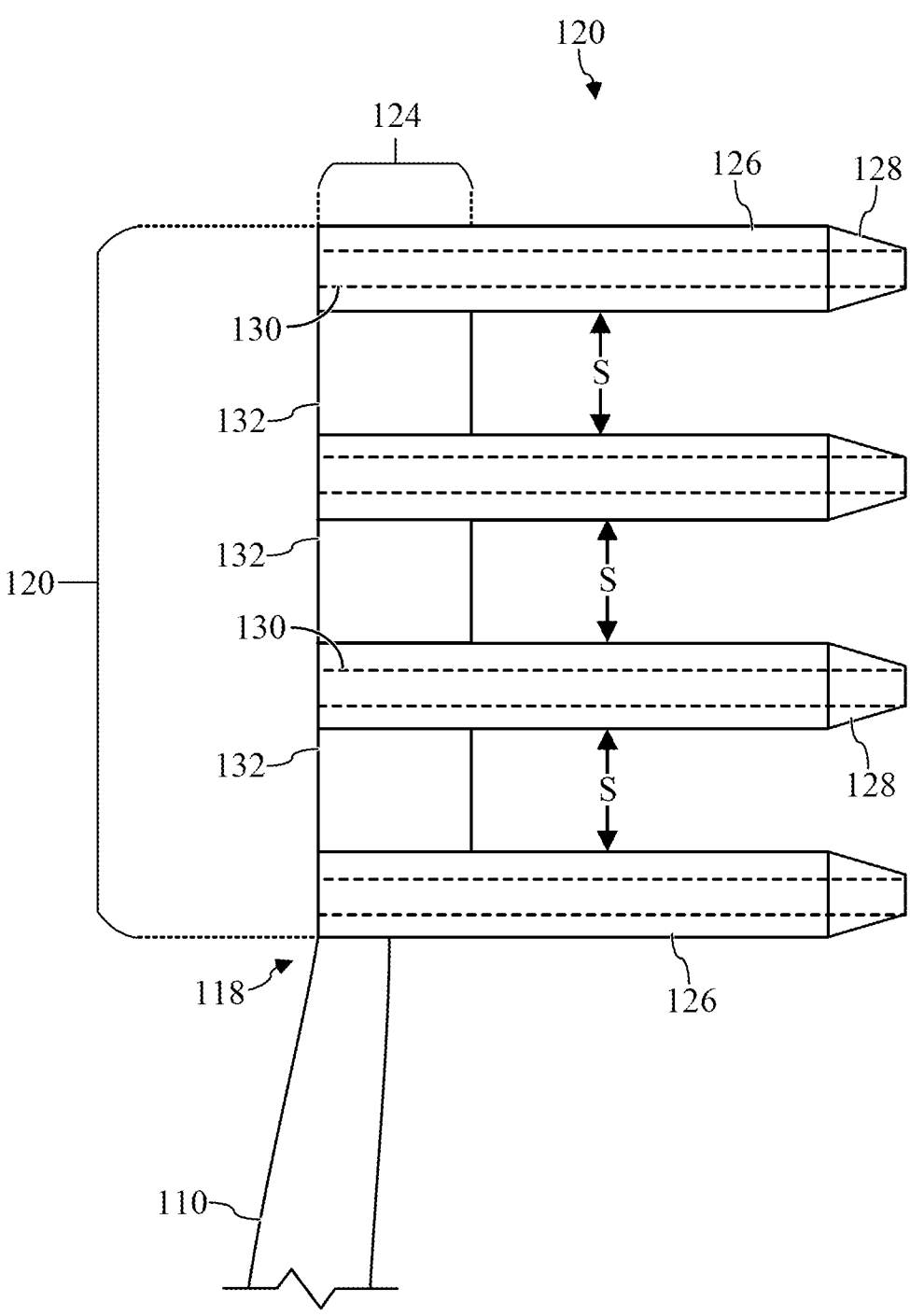
FIG. 10 shows an enlarged front view of an embodiment of surgical guide devices.
Figure 11:
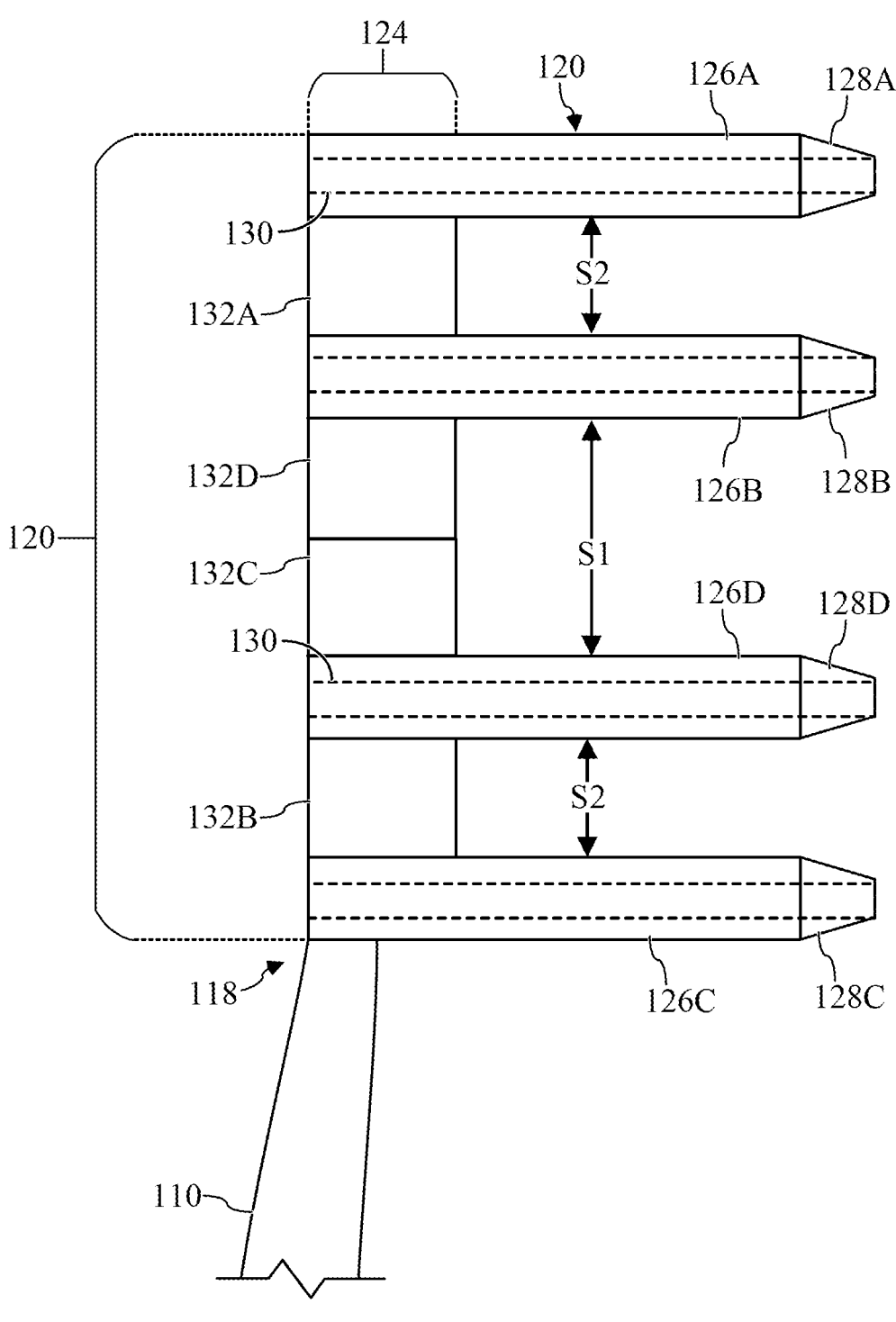
FIG. 11 shows an enlarged front view of an embodiment of surgical guide devices.

FIGS. 10 and 11 show additional non-limiting examples of surgical clamp 100 including surgical guide device 120. More specifically, FIGS. 10 and 11 shown surgical clamp 100 where surgical guide device 120 is modular and/or not integrally formed. It is understood that similarly numbered and/or named components may function in a substantially similar fashion. Redundant explanation of these components has been omitted for clarity.

As shown in the non-limiting examples, each of the plurality of guide portions 126 of surgical guide device 120 may be formed distinct from one another. Additionally, support portion 124 may be formed as and/or may include a plurality of distinct spacer members 132. Each spacer member 132 may be formed distinct from another and/or may be formed distinct from each of the plurality of guide portions 126 as well. As such, each spacer member 132 and guide portion 126 of surgical guide device 120 may be distinct from one another and may be coupled, connected, affixed, and/or attached to one another to form surgical guide device 120 of surgical clamp 100. As discussed herein, each guide portion 126 and spacer member 132 forming surgical guide device 120 of surgical clamp 100 may be coupled to one another using any suitable coupling components including, but not limited to, screws, bolts-and-nuts, rivets, snap-fit, retention bands, fastening pins, or the like.

In the non-limiting example shown in FIGS. 10 and 11, at least one spacer member 132 of the plurality of spacer members 132 may be positioned between and coupled directly to two distinct, guide portions 126 of the plurality of guide portions 126. For example, and as shown in FIG. 10, a single spacer member 132 may be positioned between each of the plurality of guide portions 126. In this example, the space (S) between each of the plurality of distinct spacer members 132 of surgical guide device 120 may be equal and/or uniform. In another non-limiting example shown in FIG. 11, a single spacer member 132A may be positioned between a top guide portion 126A and a central guide portion 126B. Additionally, a single spacer member 132B may be positioned between a bottom guide portion 126C and another central guide portion 126D. However, two distinct spacer members 132C, 132D may be coupled to one another, and may be disposed between and coupled to the two distinct, central guide portions 126B, 126D. As a result of forming surgical guide device 120 to include two distinct spacer members 132C, 132D between central guide portions 126B, 126D, central guide portions 126B, 126D may include a larger spacing (S1) between one another than a spacing (S2) between top guide portion 126A and central guide portion 126B or bottom guide portion 126C and central guide portion 126D, respectively. The tapered distal ends 128A,128B,128C,128D are also illustrated.

Although shown as being formed to include a single, uniform dimension (e.g., height), it is understood that spacer members 132 may be formed to include any predetermined dimension or size. As such, in another non-limiting example (not shown), a single spacer member 132 having a dimension/height equal to two spacer members 132C, 132D may be formed between central guide portions 126B, 126D to space (S1) the central guide portions 126B, 126D as desired.

In operation, the surgeon applies the device to posterior aspect of the bone (femur 10) of the greater trochanter on the proximal femur 10 during an openly exposed hip procedure, clamps in desired position, locks the device in place, and then first drills holes from superficial to deep through the greater trochanter 18 from superficial anterior to deep posterior through each of four individual cannulated guides 126, then through these same holes 26 in the same direction (after retraction of the drill bit 24), a straight Hewson type suture passer 28 is passed so that the loop (such as suture 30) is visible deep and posterior to the greater trochanter where sutures previously placed within the soft tissues to be repaired (in this case the short external rotator muscles and the posterior hip capsule). The suture can be placed within the loop of the Hewson passer and then pulled through from deep posterior to superficial anterior where they can be tied over the top of the lateral aspect of the intact greater trochanteric bone, thus securing the soft tissues to the bone.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the invention for various embodiments with various modifications as are suited to the particular use contemplated.

What is claimed is:

1. A surgical guide device, comprising:
   a body affixed to an end of an arm of a surgical clamp, the body including:
      a support portion;
      a plurality of guide portions extending perpendicularly from the support portion, the plurality of guide portions include:
         a first guide portion extending perpendicularly from the support portion, the first guide portion formed directly adjacent to the end of the arm of the surgical clamp, and
         at least one distinct guide portion extending perpendicularly from the support portion, the at least one distinct guide portion spaced apart from the first guide portion and formed proximate the end of the arm of the surgical clamp, wherein the first guide portion is positioned between the end of the single arm of the surgical clamp and the at least one distinct guide portion; and a plurality of apertures, each of the plurality of apertures extending through the support portion and a single, guide portion of the plurality of guide portions.

2. The surgical guide device of claim 1, wherein each of the plurality of guide portions includes a tapered distal end formed opposite the support portion.

3. The surgical guide device of claim 1, wherein each of the plurality of apertures are sized to receive a surgical drill.

4. The surgical guide device of claim 1, wherein the body is formed from a metal material, a metal alloy material, a polymer material, or a ceramic material.

5. The surgical guide device of claim 1, wherein the plurality of guide portions is integrally formed with the support portion.

6. The surgical guide device of claim 1, wherein each guide portion of the plurality of guide portions extend on opposite sides of the support portion.

7. A surgical clamp, comprising:

a first arm including a retention component; and a second arm coupled to the first arm, the second arm including a surgical guide device formed on an end of the second arm, adjacent the retention component of the first arm, wherein the surgical guide device includes:

a body including:

a support portion extending from the end of the second arm;

a plurality of guide portions extending perpendicularly from the support portion, each of plurality of guide portions spacee apart from one another and are spaced apart from the end of the second arm at distinct distances; and a plurality of apertures, each of the plurality of apertures extending through the support potion and a single, guide portion of the plurality of guide portions.

8. The surgical clamp of claim 7, wherein the surgical guide device is formed integral with the second arm.

9. The surgical clamp of claim 7, wherein the first arm is pivotably coupled to the second arm.

10. The surgical clamp of claim 7, wherein each of the plurality of guide portions of the surgical guide device includes a tapered distal end formed opposite the support portion.

11. The surgical clamp of claim 7, wherein each of the plurality of apertures of the surgical guide device are sized to receive a surgical drill.

12. The surgical clamp of claim 7, wherein the body of the surgical guide device is formed from a metal material, a metal alloy material, a polymer material, or a ceramic material.

13. A surgical clamp, comprising:

a first arm including a retention means for retaining the clamp to a bone of a patient; and a second arm coupled to the first arm, the second arm including a surgical guide means for guiding surgical tools into the bone, wherein the surgical guide means is formed on an end of the second arm and includes:

a body including:

a support portion; and a tool guide means extending perpendicularly from the support portion, the tool guide means including guide portions spaced apart from one another and are spaced apart from the end of the second arm at distinct distances, wherein the tool guide means are configured to selectively guide surgical tools into the bone.

14. The surgical clamp of claim 13, wherein the tool guide means is further configured to receive a surgical drill as a surgical tool.

* * * * *